US012402882B2

(12) United States Patent
Huang (10) Patent No.: US 12,402,882 B2
(45) Date of Patent: Sep. 2, 2025

(54) BLOOD VESSEL ANASTOMOSIS SET (71) Applicant: VASOCOLLAR INC., Tainan (TW)

(72) Inventor: Hsin-Lei Huang, Taipei (TW)

(73) Assignee: VasoCollar Inc., Tainan (TW)

( * ) Notice: Subject to any disclaimer, the term of this patent is extended or adjusted under 35 U.S.C. 154(b) by 1106 days.

(21) Appl. No.: 16/762,883

(22) PCT Filed: Oct. 29, 2018

(86) PCT No.: PCT/CN2018/112465
§ 371 (c)(1),
(2) Date: May 3, 2021

(87) PCT Pub. No.: WO2019/091303
PCT Pub. Date: May 16, 2019

(65) Prior Publication Data
US 2021/0259690 A1  Aug. 26, 2021

Related U.S. Application Data (60) Provisional application No. 62/584,724, filed on Nov. 10, 2017.

(51) Int. Cl.
A61B 17/11 (2006.01)
(52) U.S. Cl.
CPC ....... A61B 17/11 (2013.01); A61B 2017/1107 (2013.01); A61B 2017/1132 (2013.01)
(58) Field of Classification Search
CPC ............ A61B 17/11; A61B 2017/1107; A61B 2017/1132
See application file for complete search history.

(56) References Cited

U.S. PATENT DOCUMENTS 3,316,914 A * 5/1967 Collito .................. A61B 17/11
227/19
4,654,028 A * 3/1987 Suma ..................... A61B 90/00
606/198
(Continued)

FOREIGN PATENT DOCUMENTS

CN 101043851 A 9/2007
CN 101815473 A 8/2010
(Continued)

OTHER PUBLICATIONS

The International Search Report for International Application No. PCT/CN2018/112465.

Primary Examiner — Alexander J Orkin
(74) Attorney, Agent, or Firm — Haverstock & Owens, A Law Corporation (57) ABSTRACT A blood vessel anastomosis set for anastomosing a blood vessel cut of a blood vessel is provided. The blood vessel anastomosis set includes: a blood vessel anastomosis device having a plurality of anastomosis needles and a plurality of anastomosis needle holes; and a blood vessel fixation device including: a blood vessel widening portion for widening the blood vessel cut; and a blood vessel fixation portion for fixing the blood vessel cut to the blood vessel anastomosis device, wherein the blood vessel anastomosis set has a protection mechanism whereby the blood vessel fixation device is not in contact with the plurality of anastomosis needles when the blood vessel cut is fixed to the blood vessel anastomosis device.

2 Claims, 13 Drawing Sheets (56) References Cited

U.S. PATENT DOCUMENTS

| | | | |
|---|---|---|---|
| 6,569,173 B1* | 5/2003 | Blatter | A61B 17/0643 |
| | | | 606/156 |
| 6,575,985 B2 | 6/2003 | Knight et al. | |
| 2002/0082625 A1* | 6/2002 | Huxel | A61B 17/115 |
| | | | 606/153 |
| 2007/0250082 A1* | 10/2007 | Kansoul | A61B 17/11 |
| | | | 606/153 |
| 2011/0152861 A1* | 6/2011 | Weisshaupt | A61B 17/115 |
| | | | 606/41 |
| 2011/0264123 A1* | 10/2011 | Borghi | A61B 17/11 |
| | | | 606/153 |
| 2013/0204275 A1 | 8/2013 | Agarwal et al. | |
| 2015/0201942 A1* | 7/2015 | Gronberg | A61B 17/1114 |
| | | | 606/153 |

FOREIGN PATENT DOCUMENTS

| | | |
|---|---|---|
| TW | 201238618 A | 10/2012 |
| WO | 2006009503 A1 | 1/2006 |

* cited by examiner

BLOOD VESSEL ANASTOMOSIS SET

BACKGROUND OF THE INVENTION

Field of the Invention

The present disclosure relates to blood vessel anastomosis sets and, more particularly, to a blood vessel anastomosis set for anastomosing a blood vessel cut.

Description of the Prior Art

Conventional surgical procedures often entail anastomosing a blood vessel which has been cut apart. For instance, a conventional procedure of reconstruction after a mastectomy entails anastomosing severed blood vessels. However, the lengthy process of suturing blood vessels is excruciating and thus risky to patients.

In view of the aforesaid drawback of the prior art, it is necessary to provide a blood vessel anastomosis set conducive to speeding up a surgical procedure of anastomosing a blood vessel cut.

SUMMARY OF THE INVENTION

In view of the aforesaid drawback of the prior art, it is an objective of the present disclosure to provide a blood vessel anastomosis set conducive to speeding up a surgical procedure of anastomosing a blood vessel cut.

In order to achieve the above and other objectives, the present disclosure provides a blood vessel anastomosis set for anastomosing a blood vessel cut of a blood vessel. The blood vessel anastomosis set comprises: a blood vessel anastomosis device having a plurality of anastomosis needles and a plurality of anastomosis needle holes; and a blood vessel fixation device, comprising: a first blood vessel widening portion for widening the blood vessel cut; and a blood vessel fixation portion for fixing the blood vessel cut to the blood vessel anastomosis device, wherein the blood vessel anastomosis set has a protection mechanism whereby the blood vessel fixation device is not in contact with the plurality of anastomosis needles when the blood vessel cut is fixed to the blood vessel anastomosis device.

In a preferred embodiment of the present disclosure, the blood vessel anastomosis device is of a ring-shaped structure and has an inner hole which the blood vessel is fitted in.

In a preferred embodiment of the present disclosure, the blood vessel anastomosis device is connected through the plurality of anastomosis needles and the plurality of anastomosis needle holes to a second blood vessel anastomosis device fixed to another blood vessel cut.

In a preferred embodiment of the present disclosure, the blood vessel anastomosis device comprises a front-end anastomosis portion and a rear-end anastomosis portion, wherein the plurality of anastomosis needles are disposed at the rear-end anastomosis portion and penetrate the front-end anastomosis portion, thereby allowing the rear-end anastomosis portion to be movably connected to the front-end anastomosis portion by the anastomosis needles.

In a preferred embodiment of the present disclosure, the protection mechanism prevents the plurality of anastomosis needles from protruding from the front-end anastomosis portion when the blood vessel fixation portion fixes the blood vessel cut to the blood vessel anastomosis device.

In a preferred embodiment of the present disclosure, the blood vessel fixation portion has a receiving portion, and the protection mechanism enables the plurality of anastomosis needles to be received in the receiving portion when the blood vessel fixation portion fixes the blood vessel cut to the blood vessel anastomosis device.

In a preferred embodiment of the present disclosure, the blood vessel fixation device further comprises a second blood vessel widening portion movably received in the blood vessel fixation device, wherein the second blood vessel widening portion widens the blood vessel from inside.

In a preferred embodiment of the present disclosure, the blood vessel fixation device further comprises a retracting portion whereby the second blood vessel widening portion restores a retracted state thereof early as soon as the second blood vessel widening portion is retracted into the blood vessel fixation device.

In a preferred embodiment of the present disclosure, the front end of the first blood vessel widening portion and/or the second blood vessel widening portion is provided with one of an inclined surface, a concave arc surface and an outward concave arc surface to gradually widening the blood vessel cut.

In a preferred embodiment of the present disclosure, the blood vessel anastomosis device has a snap-engagement portion, and the blood vessel fixation portion is separably disposed at the blood vessel fixation device, wherein, as soon as the blood vessel fixation portion fixes the blood vessel cut to the blood vessel anastomosis device, the blood vessel fixation portion is snap-engaged with the snap-engagement portion, and the blood vessel cut is clamped between the blood vessel fixation portion and the blood vessel anastomosis device.

In order to achieve the above and other objectives, the present disclosure further provides a blood vessel anastomosis set for anastomosing a blood vessel cut of a blood vessel. The blood vessel anastomosis set comprises: a blood vessel anastomosis device; and a blood vessel fixation device for widening the blood vessel cut to allow the blood vessel cut to be fitted to the blood vessel anastomosis device, wherein the blood vessel anastomosis device comprises: a front-end anastomosis portion; and a rear-end anastomosis portion having a plurality of anastomosis needles, wherein the plurality of anastomosis needles penetrate the front-end anastomosis portion, such that the rear-end anastomosis portion is movably connected to the front-end anastomosis portion through the anastomosis needles.

In a preferred embodiment of the present disclosure, the blood vessel anastomosis set is connected through the plurality of anastomosis needles to a second blood vessel anastomosis device fixed to another blood vessel cut.

In a preferred embodiment of the present disclosure, the plurality of anastomosis needles do not protrude from the front-end anastomosis portion when the blood vessel fixation device fixes the blood vessel cut to the blood vessel anastomosis device.

In a preferred embodiment of the present disclosure, the blood vessel fixation device comprises a foldable blood vessel widening portion, and the blood vessel fixation device widens the blood vessel cut through the foldable blood vessel widening portion.

The foregoing aspects and other aspects of the present disclosure are illustrated by non-restrictive specific embodiments, depicted by the accompanying drawings, and described below.

DETAILED DESCRIPTION OF THE EMBODIMENTS

Figure 1A:
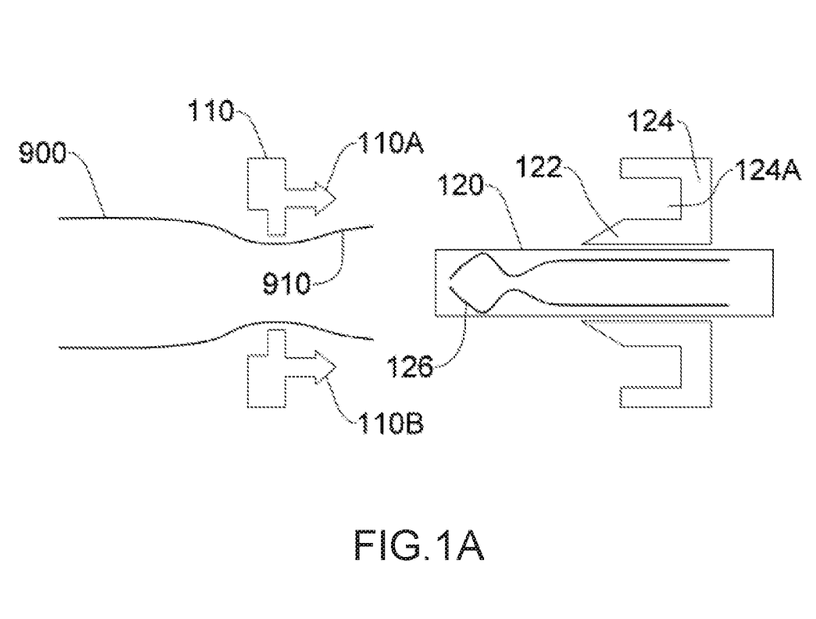
FIG. 1A is a schematic view of how to operate a blood vessel anastomosis set according to a specific embodiment of the present disclosure.

Referring to FIG. 1A through FIG. 1G, there are shown schematic views of how to operate a blood vessel anastomosis set according to a specific embodiment of the present disclosure. In the embodiment illustrated by FIG. 1A, a blood vessel anastomosis set 100 comprises a blood vessel anastomosis device 110 and a blood vessel fixation device 120. The blood vessel anastomosis device 110 has anastomosis needles 110A, 110B. The blood vessel fixation device 120 further comprises a first blood vessel widening portion 122, a blood vessel fixation portion 124 and a second blood vessel widening portion 126. The second blood vessel widening portion 126 is movably received in the blood vessel fixation device 120. The blood vessel fixation portion 124 has a receiving portion 124A, in which the receiving portion 124A is a cavity arranged on the blood vessel fixation portion 124. The front end of the first blood vessel widening portion 122 has an oblique surface for widening a blood vessel cut gradually. FIG. 1A serves an exemplary purpose only; consequently, the front end of the first blood vessel widening portion 122 is not necessarily an oblique surface but can be a concave arcuate surface or convex arcuate surface as needed to facilitate the gradual widening of the blood vessel cut.

Figure 1B:
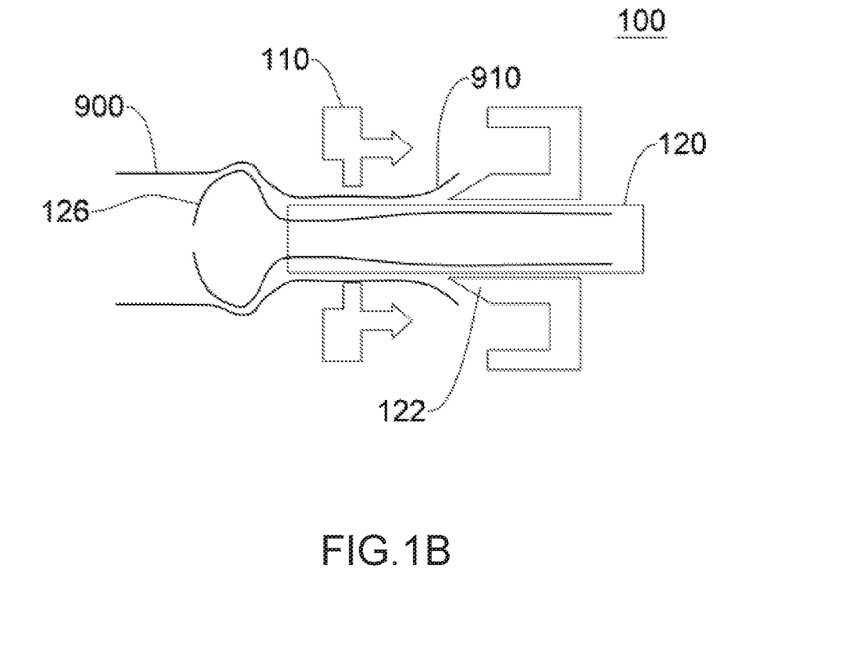
FIG. 1B is a schematic view of how to operate the blood vessel anastomosis set according to a specific embodiment of the present disclosure.
Figure 1C:
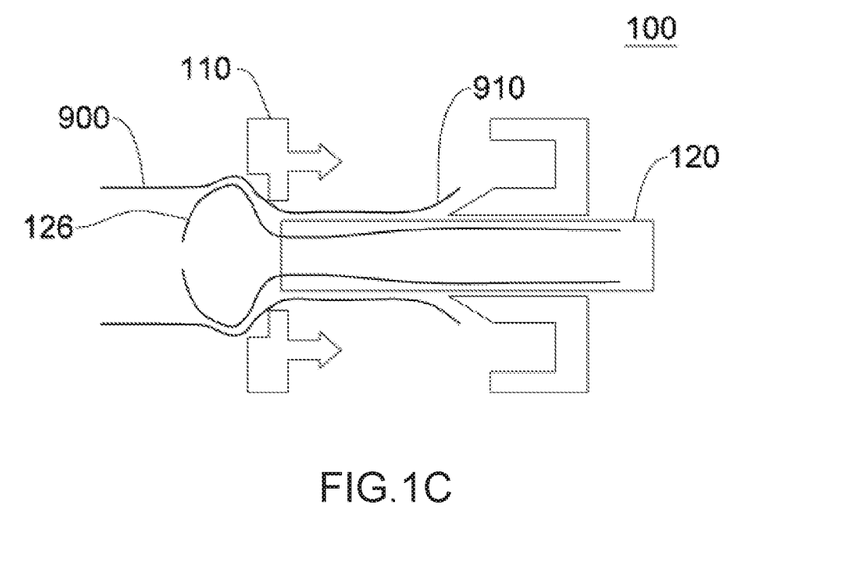
FIG. 1C is a schematic view of how to operate the blood vessel anastomosis set according to a specific embodiment of the present disclosure.

As shown in FIG. 1A, the blood vessel anastomosis device 110 of the blood vessel anastomosis set 100 is fitted around a blood vessel cut 910 of a blood vessel 900. The blood vessel anastomosis device 110 is of a ring-shaped structure; consequently, the blood vessel cut 910 can penetrate the inner hole of the blood vessel anastomosis device 110. Referring to FIG. 1B, after the blood vessel anastomosis device 110 has been fitted around the blood vessel cut 910 of the blood vessel 900, the front end of the blood vessel fixation device 120 is inserted through the blood vessel cut 910 into the blood vessel 900, whereas the blood vessel fixation device 120 in the blood vessel 900 penetrates the inner hole of the blood vessel anastomosis device 110. Then, the second blood vessel widening portion 126 is protruded from the front end of the blood vessel fixation device 120, such that the second blood vessel widening portion 126 is inserted into the blood vessel 900. At this point in time, the second blood vessel widening portion 126 spreads and widens the blood vessel 900 from inside. Referring to FIG. 1C, after the second blood vessel widening portion 126 has widened the blood vessel 900 from inside, the blood vessel fixation device 120 is moved backward (i.e., toward the blood vessel cut 910), such that the wall of the blood vessel 900 is clamped by and between the second blood vessel widening portion 126 and the blood vessel anastomosis device 110, thereby allowing the blood vessel 900 to be temporarily fixed in place while an anastomosis procedure is being performed thereon.

Figure 1D:
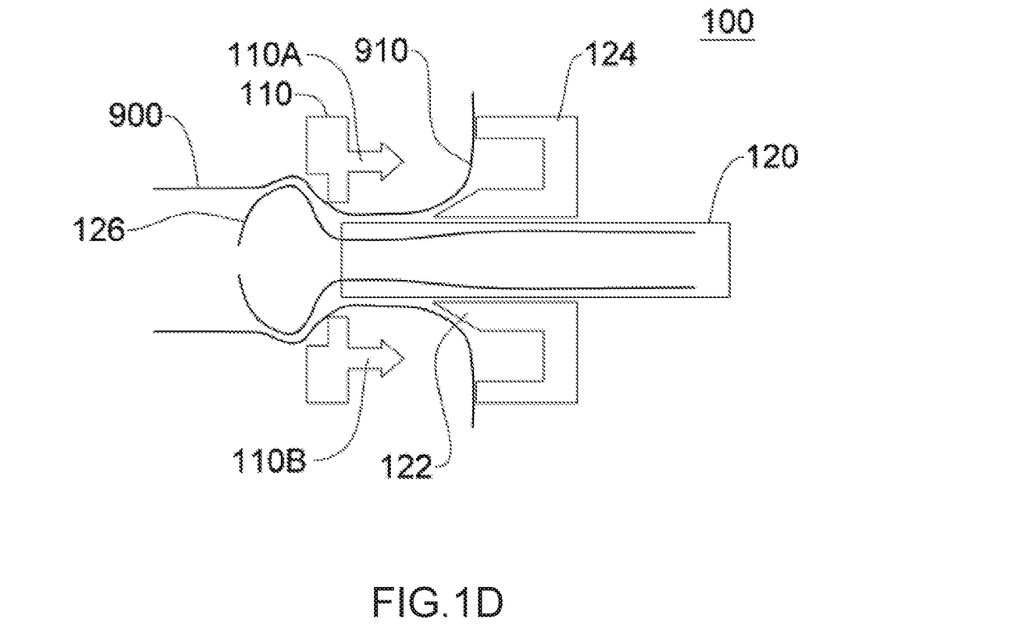
FIG. 1D is a schematic view of how to operate the blood vessel anastomosis set according to a specific embodiment of the present disclosure.
Figure 1E:
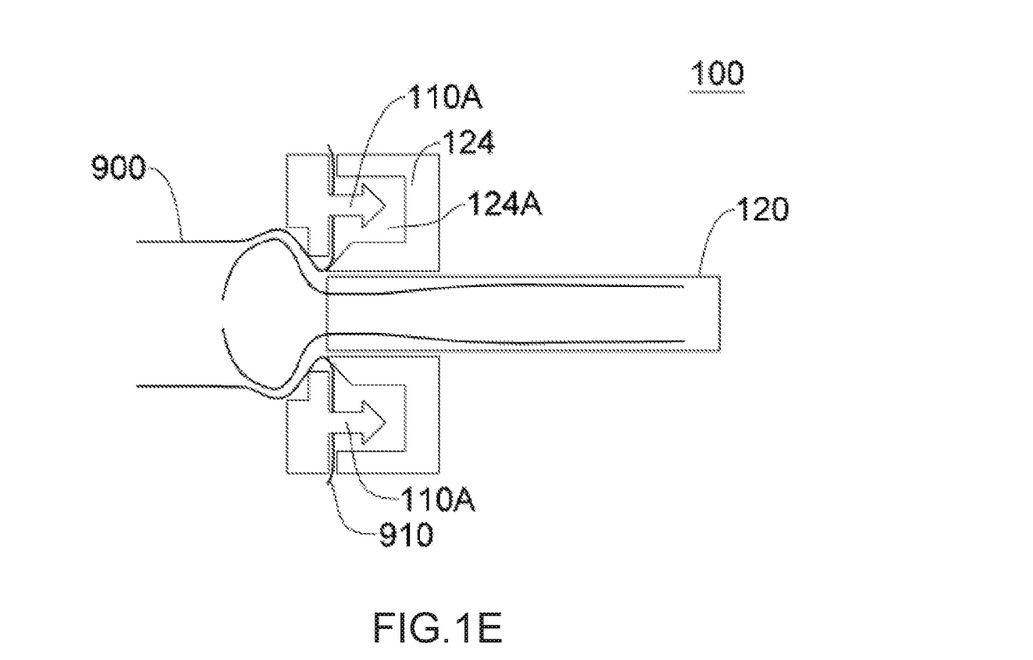
FIG. 1E is a schematic view of how to operate the blood vessel anastomosis set according to a specific embodiment of the present disclosure.

Referring to FIG. 1D, after the blood vessel 900 has been temporarily fixed in place with the second blood vessel widening portion 126, the first blood vessel widening portion 122 is manipulated in such a manner to cause the front end of the first blood vessel widening portion 122 to enter the blood vessel cut 910 (i.e., move toward the blood vessel cut 910); consequently, the first blood vessel widening portion 122 widens the blood vessel cut 910 gradually and allows the blood vessel cut 910 to come into contact with the blood vessel fixation portion 124. Then, the first blood vessel widening portion 122 is manipulated continuously in such a manner to fix the blood vessel cut 910 to the anastomosis needles 110A, 110B of the blood vessel anastomosis device 110 (as shown in FIG. 1E) with the blood vessel fixation portion 124. At this point in time, the anastomosis needles 110A, 110B are received in the receiving portion 124A. During the anastomosis procedure, the blood vessel fixation device 120 is not in contact with the anastomosis needles 110A, 110B to preclude the chance that the anastomosis needles 110A, 110B may be compressed by the blood vessel fixation device 120 and thus damaged. In a specific embodiment, the anastomosis needles 110A, 110B has barbs whereby the blood vessel cut 910 is fixed to the anastomosis needles 110A, 110B firmly.

Figure 1F:
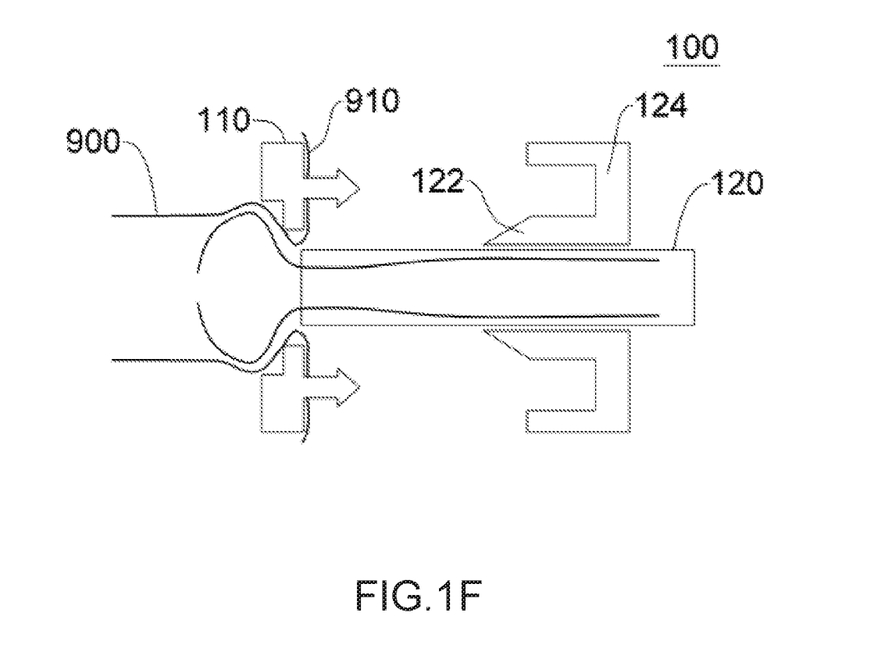
FIG. 1F is a schematic view of how to operate the blood vessel anastomosis set according to a specific embodiment of the present disclosure.
Figure 1G:
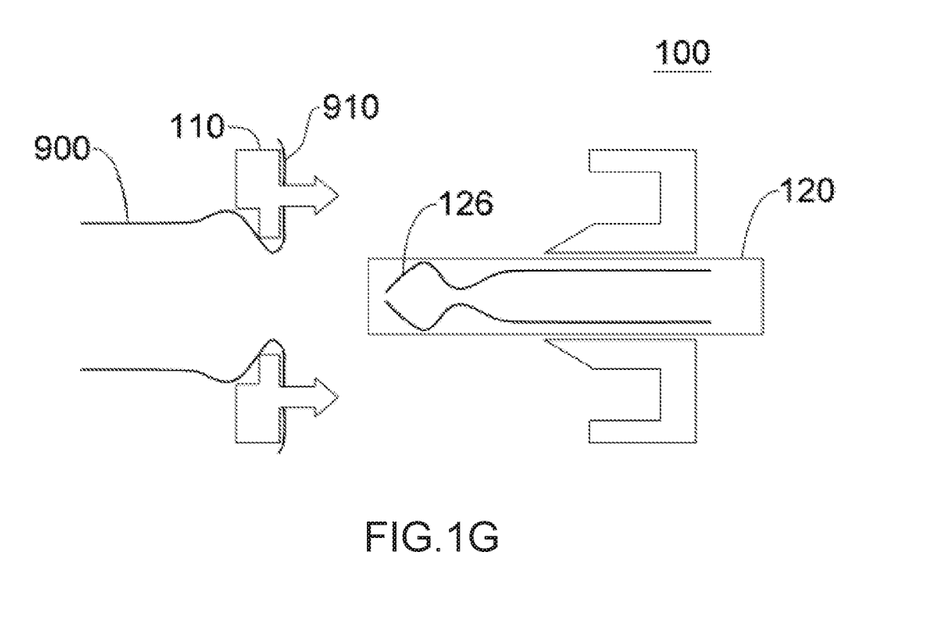
FIG. 1G is a schematic view of how to operate the blood vessel anastomosis set according to a specific embodiment of the present disclosure.

Referring to FIG. 1F, after the blood vessel cut 910 has been fixed to the anastomosis needles 110A, 110B of the blood vessel anastomosis device 110, the first blood vessel widening portion 122 is manipulated in such a manner to be moved away from the blood vessel cut 910. Referring to FIG. 1G, as soon as the first blood vessel widening portion 122 is moved away from the blood vessel cut 910, the second blood vessel widening portion 126 is retracted into the blood vessel fixation device 120, and the blood vessel fixation device 120 is moved out of the blood vessel cut 910. In a specific embodiment, the step shown in FIG. 1F is dispensed with, that is, the second blood vessel widening portion 126 is retracted into the blood vessel fixation device 120 directly, and the blood vessel fixation device 120 is moved out of the blood vessel cut 910, thereby dispensing the need to manipulate the first blood vessel widening portion 122 in such a manner to cause the first blood vessel widening portion 122 to move in a direction away from the blood vessel cut 910.

Figure 2:
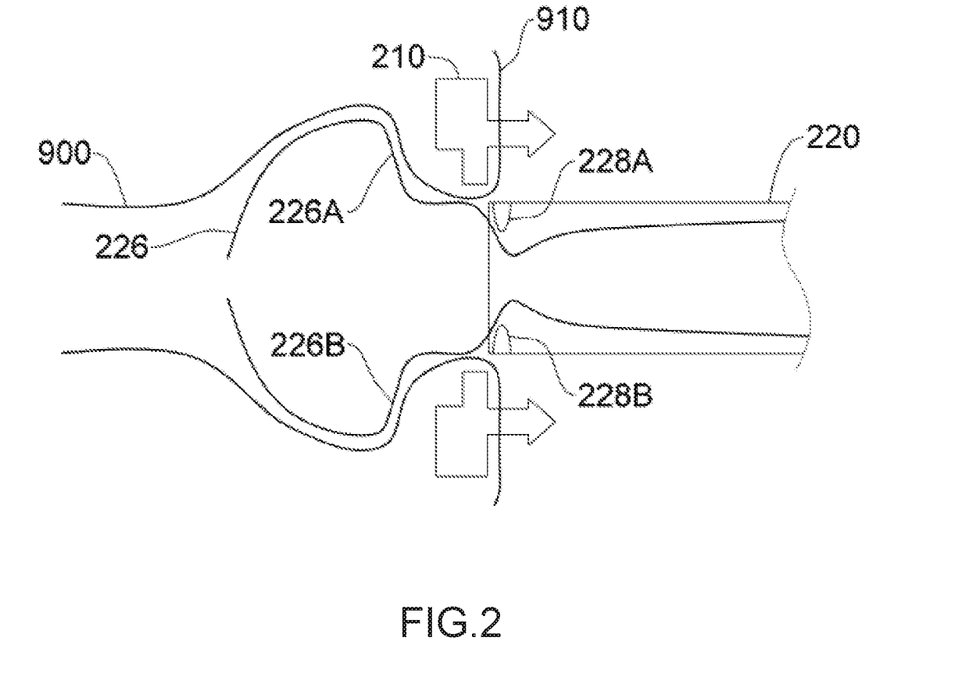
FIG. 2 is a schematic view of a blood vessel fixation device comprising a second blood vessel widening portion according to a specific embodiment of the present disclosure.

Referring to FIG. 2, there is shown a schematic view of a blood vessel fixation device comprising a second blood vessel widening portion according to a specific embodiment of the present disclosure. In the embodiment illustrated by FIG. 2, a blood vessel fixation device 220 further comprises retracting portions 228A, 228B, in which the retracting portions 228A, 228B are humps arranged in the blood vessel fixation device 220. Each retracting portion is corresponding to a respective blood vessel widening portion, and therefore, as soon as a second blood vessel widening portion 226 is retracted into the blood vessel fixation device 220, the retracting portions 228A, 228B cause the second blood vessel widening portion 226 to restore a retracted state thereof early. Therefore, the retraction of the second blood vessel widening portion 226 into the blood vessel fixation device 220 precludes the chance that the wall of the blood vessel 900 may be excessively compressed by clamping portions 226A, 226B of the second blood vessel widening portion 226 and a blood vessel anastomosis device 210 and thus damaged.

Figure 3:
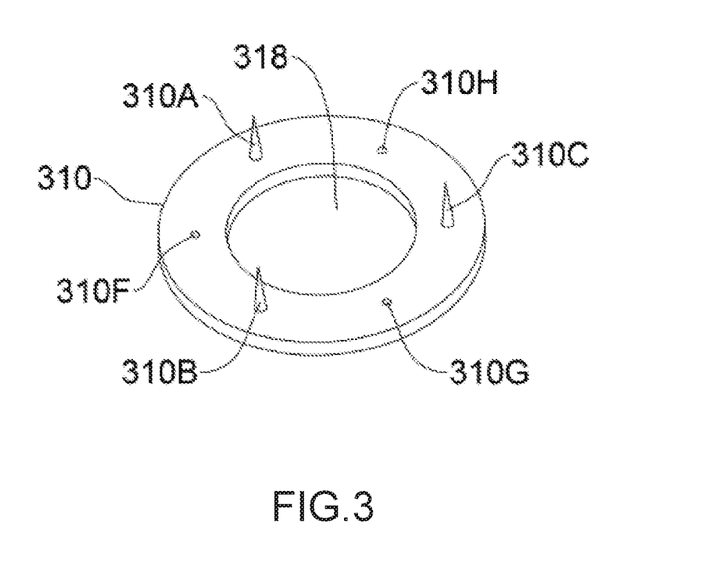
FIG. 3 is a schematic view of a blood vessel anastomosis device according to a specific embodiment of the present disclosure.

Referring to FIG. 3, there is a schematic view of a blood vessel anastomosis device according to a specific embodiment of the present disclosure. In the embodiment illustrated by FIG. 3, a blood vessel anastomosis device 310 is of a ring-shaped structure and has an inner hole 318. Therefore, the blood vessel can penetrate the inner hole 318. The blood vessel anastomosis device 310 has anastomosis needles 310A, 310B, 310C and anastomosis needle holes 310F, 310G, 310H. Therefore, after a first blood vessel anastomosis device and a second blood vessel anastomosis device have been fixed to two blood vessel cuts, respectively, the anastomosis needles of the first blood vessel anastomosis device are inserted into the anastomosis needle holes of the second blood vessel anastomosis device, and the anastomosis needles of the second blood vessel anastomosis device are separably inserted into the anastomosis needle holes of the first blood vessel anastomosis device, thereby connecting the two blood vessel cuts to each other.

Figure 4:
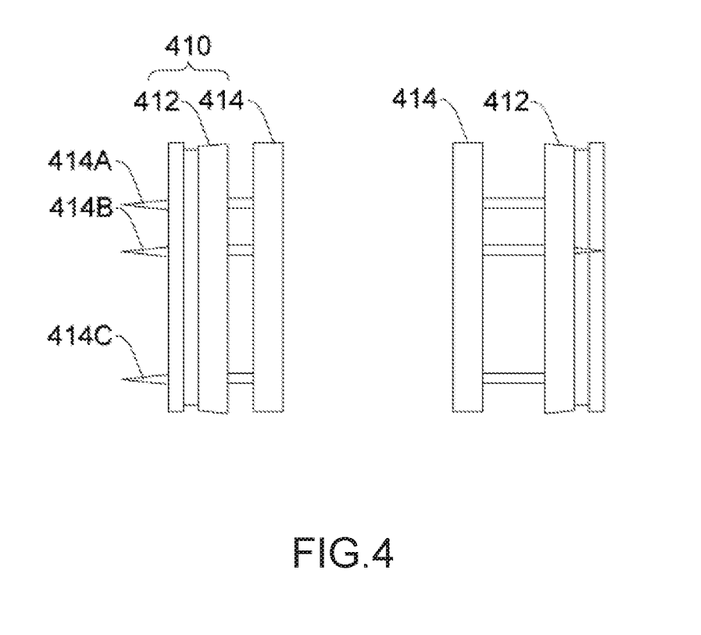
FIG. 4 is a schematic view of a blood vessel anastomosis device according to another specific embodiment of the present disclosure.

Referring to FIG. 4, there is shown a schematic view of a blood vessel anastomosis device according to another specific embodiment of the present disclosure. In the embodiment illustrated by FIG. 4, a blood vessel anastomosis device 410 comprises a front-end anastomosis portion 412 and a rear-end anastomosis portion 414. The rear-end anastomosis portion 414 has anastomosis needles 414A, 414B, 414C. The anastomosis needles 414A, 414B, 414C penetrate the front-end anastomosis portion 412, such that the rear-end anastomosis portion 414 is movably connected to the front-end anastomosis portion 412 through the anastomosis needles 414A, 414B, 414C. In a specific embodiment, the front-end anastomosis portion 412 and the rear-end anastomosis portion 414 each have anastomosis needle holes. In another specific embodiment, only the front-end anastomosis portion 412 has anastomosis needle holes. Therefore, the first blood vessel anastomosis device and the second blood vessel anastomosis device, which are fixed to different blood vessel cuts, respectively, are connected to each other through the anastomosis needles and the anastomosis needle holes.

Referring to FIG. 5A through FIG. 5E, there are shown schematic views of how to operate the blood vessel anastomosis set according to another specific embodiment of the present disclosure. In the embodiment illustrated by FIG. 5A, a blood vessel anastomosis set 500 comprises a blood vessel anastomosis device 510 and a blood vessel fixation device 520. The blood vessel anastomosis device 510 further comprises a front-end anastomosis portion 512 and a rear-end anastomosis portion 514. The blood vessel fixation device 520 further comprises a blood vessel widening portion 522 and a blood vessel fixation portion 524. The blood vessel fixation portion 524 is separably disposed at the blood vessel fixation device 520. In this specific embodiment, the rear-end anastomosis portion 514 has anastomosis needles 514A, 514B. The anastomosis needles 514A, 514B penetrate the front-end anastomosis portion 512, such that the rear-end anastomosis portion 514 is movably connected to the front-end anastomosis portion 512 through the anastomosis needles 514A, 514B. The front-end anastomosis portion 512 of the blood vessel anastomosis device 510 has a snap-engagement portion 512A. The blood vessel fixation portion 524 is snap-engaged with the snap-engagement portion 512A.

Figure 5A:
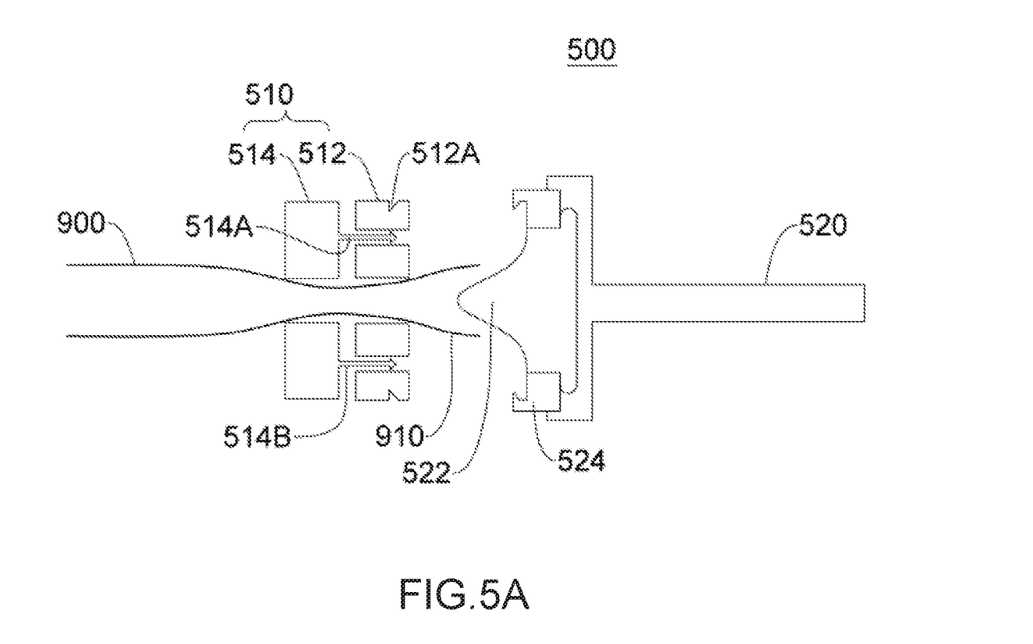
FIG. 5A is a schematic view of how to operate the blood vessel anastomosis set according to another specific embodiment of the present disclosure.
Figure 5B:
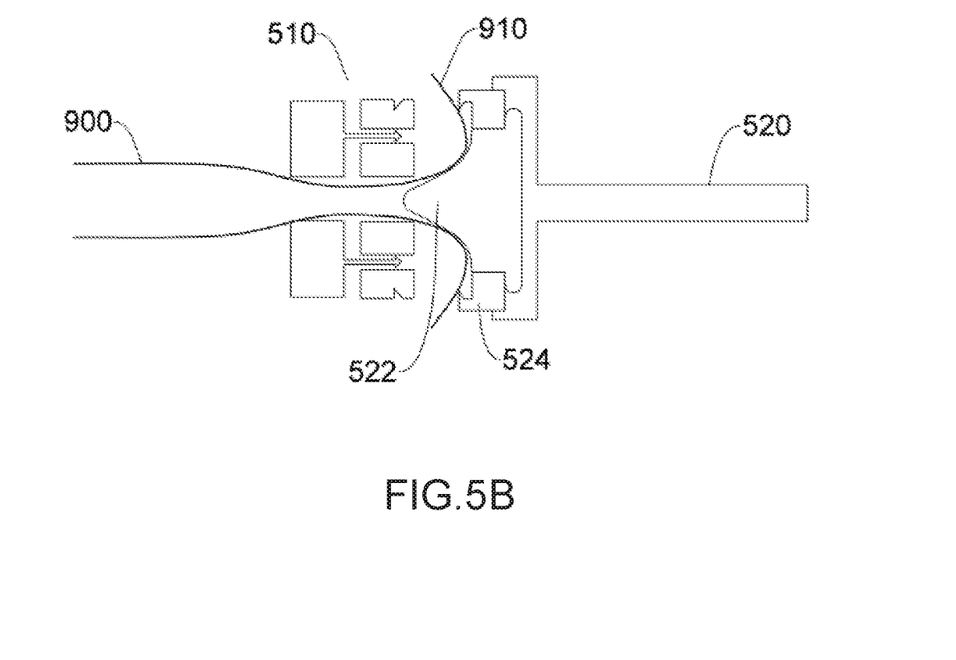
FIG. 5B is a schematic view of how to operate the blood vessel anastomosis set according to another specific embodiment of the present disclosure.

Operation of the blood vessel anastomosis set according to another specific embodiment illustrated by FIG. 5A through FIG. 5E is described below. Referring to FIG. 5A, the blood vessel anastomosis device 510 of the blood vessel anastomosis set 500 is fitted around the blood vessel cut 910 of the blood vessel 900. The blood vessel anastomosis device 510 is of a ring-shaped structure; consequently, the blood vessel cut 910 penetrates the inner hole of the blood vessel anastomosis device 510. Referring to FIG. 5B, after the blood vessel anastomosis device 510 has been fitted around the blood vessel cut 910 of the blood vessel 900, the blood vessel fixation device 520 is manipulated in such a manner to cause the front end of the blood vessel widening portion 522 to enter the blood vessel cut 910 (i.e., move toward the blood vessel cut 910); consequently, the blood vessel widening portion 522 widens the blood vessel cut 910 gradually and allows the blood vessel cut 910 to come into contact with the blood vessel fixation portion 524.

Figure 5C:
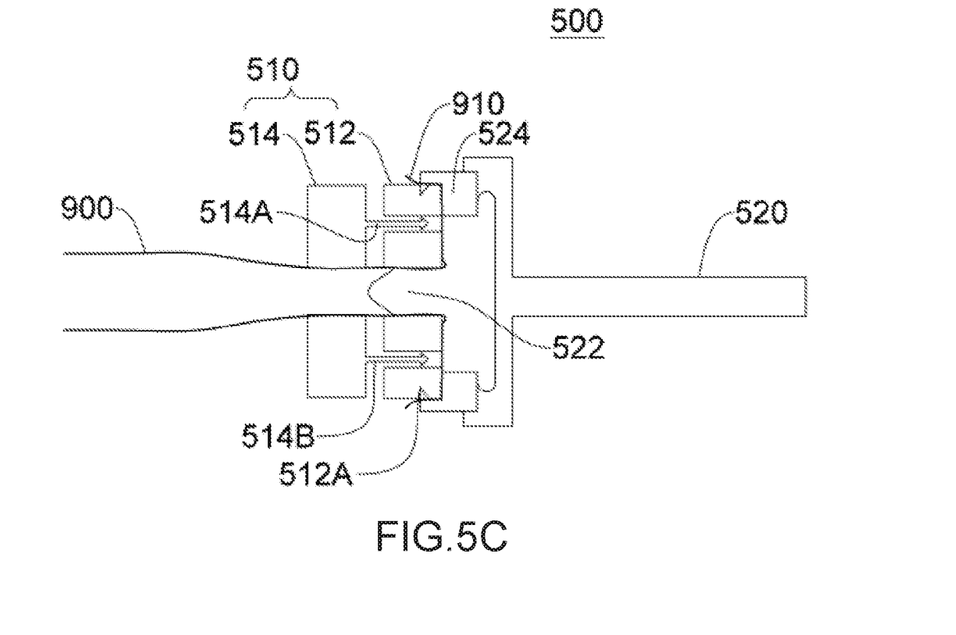
FIG. 5C is a schematic view of how to operate the blood vessel anastomosis set according to another specific embodiment of the present disclosure.

Referring to FIG. 5C, after the blood vessel cut 910 has come into contact with the blood vessel fixation portion 524, the blood vessel fixation device 520 is manipulated continuously so as for the blood vessel fixation portion 524 to be snap-engaged with the snap-engagement portion 512A of the front-end anastomosis portion 512 and for the blood vessel cut 910 to be clamped between the blood vessel fixation portion 524 and the front-end anastomosis portion 512 of the blood vessel anastomosis device 510. Consequently, the blood vessel fixation portion 524 can fix the blood vessel cut 910 to the blood vessel anastomosis device 510. After the blood vessel fixation portion 524 has fixed the blood vessel cut 910 to the blood vessel anastomosis device 510, the anastomosis needles 514A, 514B do not protrude from the front-end anastomosis portion 512. Therefore, the anastomosis needles 514A, 514B are unlikely to be compressed by the blood vessel fixation device 520 and damaged.

In a specific embodiment, the blood vessel widening portion 522 is made of a deformable material. Therefore, during the anastomosis procedure, the blood vessel widening portion 522 corresponds in shape to the blood vessel anastomosis device 510 and thus pushes the blood vessel cut 910 toward the blood vessel widening portion 522.

Figure 5D:
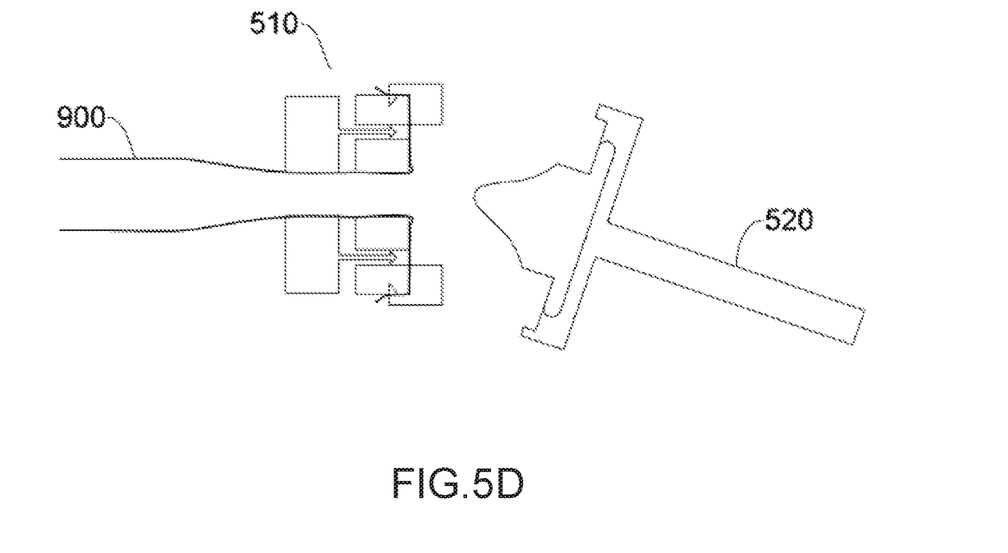
FIG. 5D is a schematic view of how to operate the blood vessel anastomosis set according to another specific embodiment of the present disclosure.
Figure 5E:
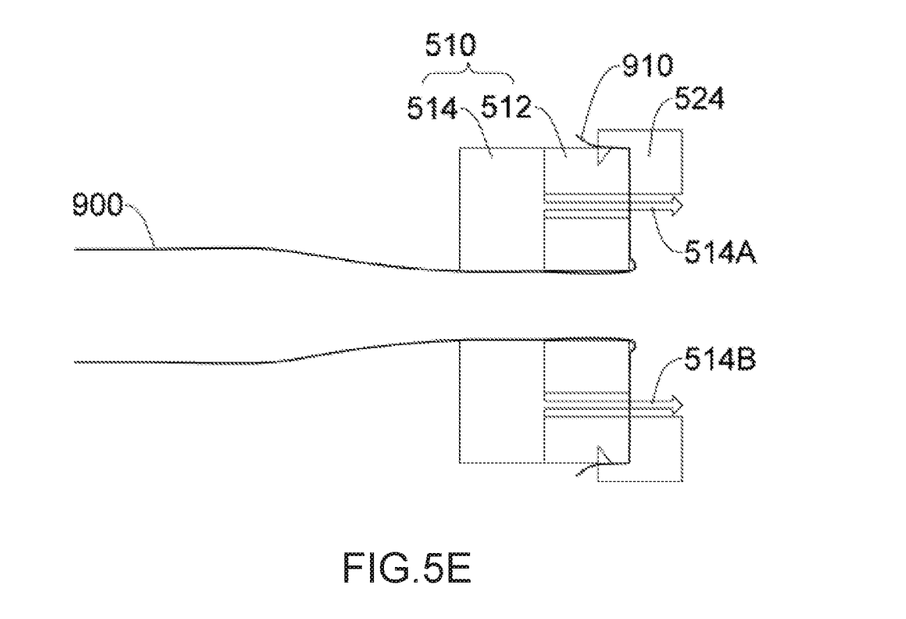
FIG. 5E is a schematic view of how to operate the blood vessel anastomosis set according to another specific embodiment of the present disclosure.

Referring to FIG. 5D, after blood vessel fixation portion 524 has fixed the blood vessel cut 910 to the blood vessel anastomosis device 510, the blood vessel fixation device 520 is removed. Then, the rear-end anastomosis portion 514 is pushed toward the front-end anastomosis portion 512; consequently, the rear-end anastomosis portion 514 abuts against the front-end anastomosis portion 512, and the anastomosis needles 514A, 514B penetrate the blood vessel cut 910 to thereby protrude from the front-end anastomosis portion 512 (as shown in FIG. 5E). Therefore, the blood vessel cut 910 is fixed to the blood vessel anastomosis device 510 firmly.

Figure 6:
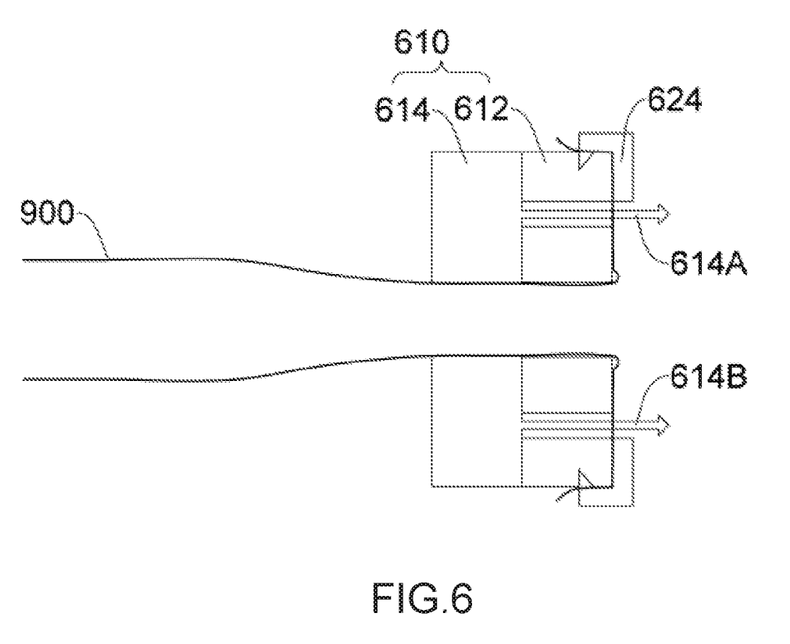
FIG. 6 is a schematic view of a blood vessel fixation portion is snap-engaged with a blood vessel anastomosis device according to a specific embodiment of the present disclosure.

Referring to FIG. 6, there is shown a schematic view of a blood vessel fixation portion is snap-engaged with a blood vessel anastomosis device according to a specific embodiment of the present disclosure. In the embodiment illustrated by FIG. 6, upon fixation of the blood vessel cut 910 to a blood vessel anastomosis device 610, penetration of anastomosis needles 614A, 614B into the blood vessel cut 910 and protrusion of the anastomosis needles 614A, 614B from a front-end anastomosis portion 612, the anastomosis needles 614A, 614B protrude from a blood vessel fixation portion 624. Therefore, as soon as a first blood vessel anastomosis device and a second blood vessel anastomosis device are fixed to two blood vessel cuts, respectively, the two blood vessel cuts are connected to each other through the anastomosis needles of the first blood vessel anastomosis device and the anastomosis needles of the second blood vessel anastomosis device.

Referring to FIG. 7A through FIG. 7F, there are shown schematic views of how to operate the blood vessel anastomosis set according to yet another specific embodiment of the present disclosure. In the embodiment illustrated by FIG. 7A, the blood vessel anastomosis set 700 comprises a blood vessel anastomosis device 710 and a blood vessel fixation device 720. The blood vessel anastomosis device 710 further comprises a front-end anastomosis portion 712 and a rear-end anastomosis portion 714. The rear-end anastomosis portion 714 has anastomosis needles 714A, 714B. The anastomosis needles 714A, 714B penetrate the front-end anastomosis portion 712, such that the rear-end anastomosis portion 714 is movably connected to the front-end anastomosis portion 712 through the anastomosis needles 714A, 714B.

Figure 7A:
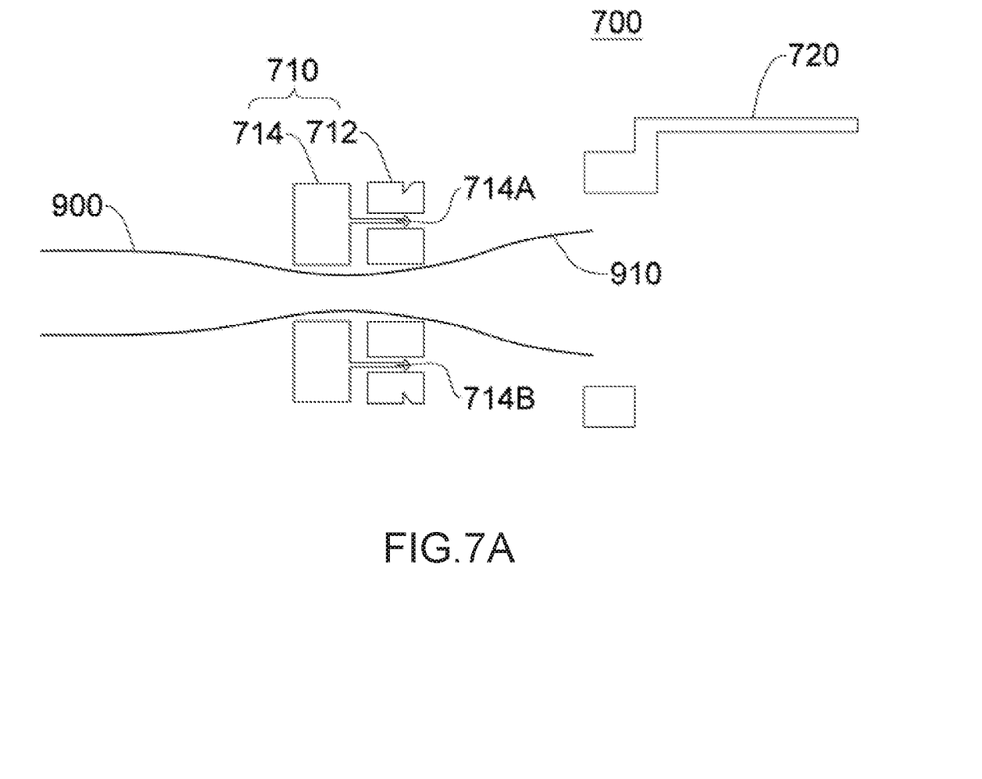
FIG. 7A is a schematic view of how to operate the blood vessel anastomosis set according to yet another specific embodiment of the present disclosure.
Figure 7B:
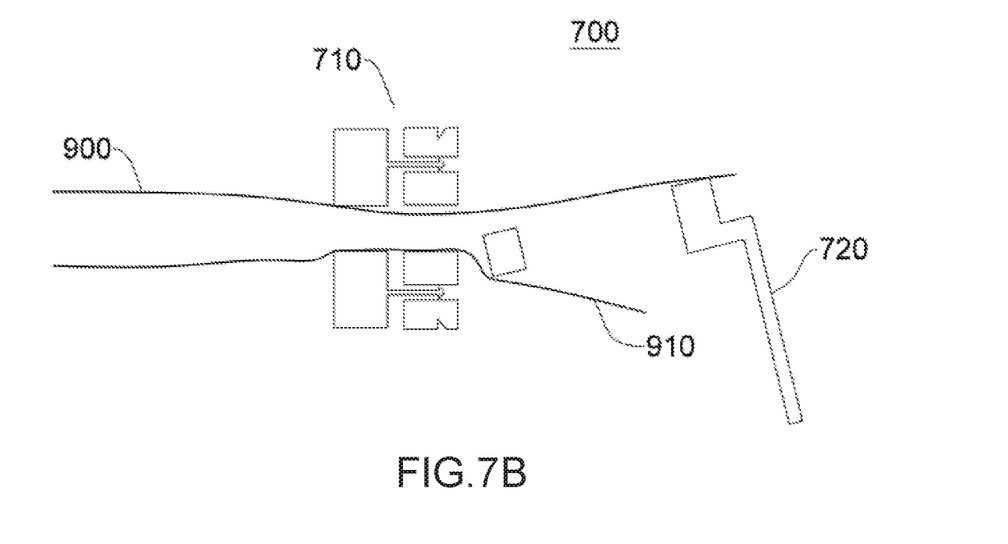
FIG. 7B is a schematic view of how to operate the blood vessel anastomosis set according to yet another specific embodiment of the present disclosure.

The anastomosis procedure performed according to the specific embodiment illustrated by FIG. 7A through FIG. 7F is described below. Referring to FIG. 7A, the blood vessel anastomosis device 710 of the blood vessel anastomosis set 700 is fitted around the blood vessel cut 910 of the blood vessel 900. The blood vessel anastomosis device 710 is of a ring-shaped structure; consequently, the blood vessel cut 910 penetrates the inner hole of the blood vessel anastomosis device 710. Referring to FIG. 7B, as soon as the blood vessel anastomosis device 710 is fitted around the blood vessel cut 910, the blood vessel fixation device 720 enters the blood vessel cut 910 by an entering angle.

Figure 7C:
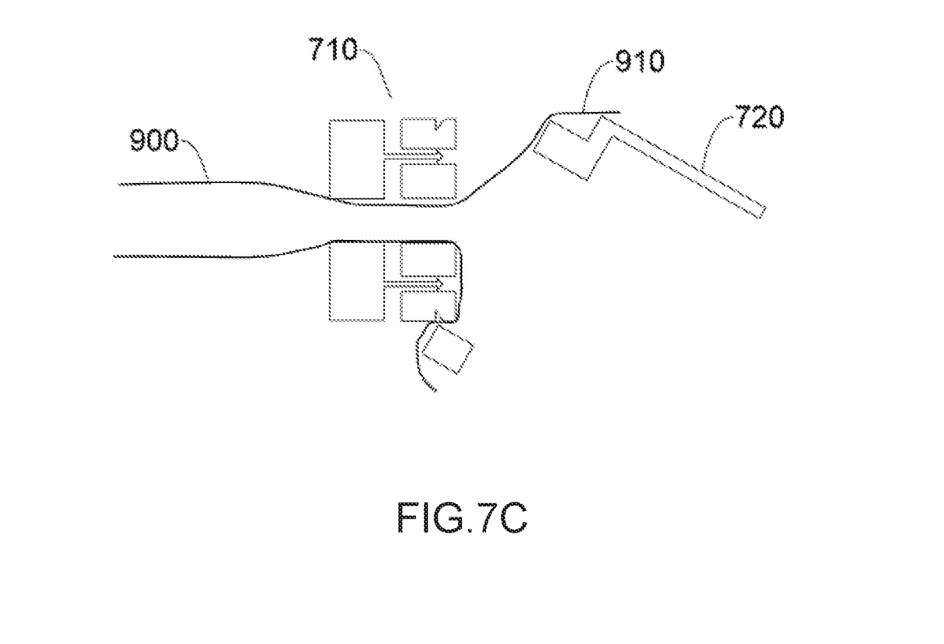
FIG. 7C is a schematic view of how to operate the blood vessel anastomosis set according to yet another specific embodiment of the present disclosure.
Figure 7D:
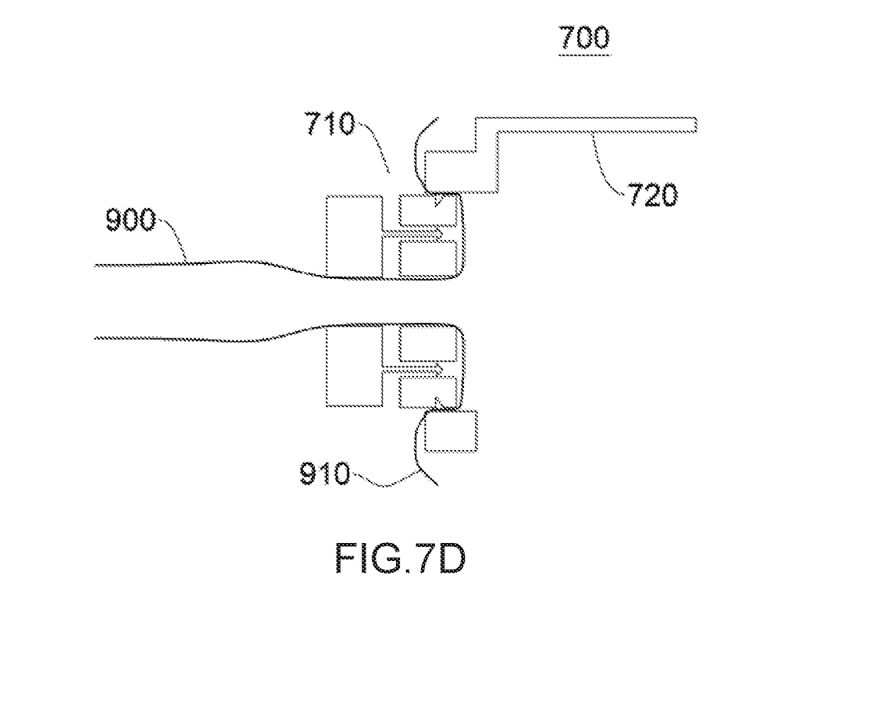
FIG. 7D is a schematic view of how to operate the blood vessel anastomosis set according to yet another specific embodiment of the present disclosure.

Referring to FIG. 7C, after the front end of the blood vessel fixation device 720 has entered the blood vessel cut 910, the blood vessel fixation device 720 is manipulated to adjust its entering angle, such that the front end of the blood vessel fixation device 720 widens the blood vessel cut 910. Then, the blood vessel fixation device 720 is manipulated to adjust its entering angle, such that the widened blood vessel cut 910 is fitted to the blood vessel anastomosis device 710 (as shown in FIG. 7D). At this point in time, instead of removing blood vessel fixation device 720, it is necessary to manipulate the blood vessel fixation device 720 in such a manner to press the blood vessel cut 910 slightly and thus prevent the blood vessel cut 910 from slipping out of the blood vessel anastomosis device 710.

Figure 7E:
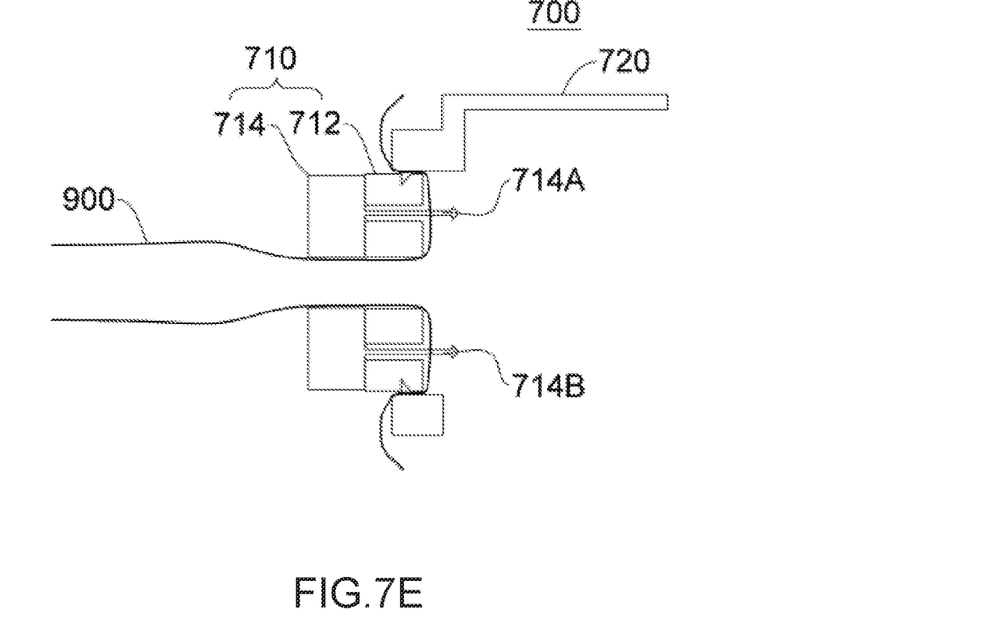
FIG. 7E is a schematic view of how to operate the blood vessel anastomosis set according to yet another specific embodiment of the present disclosure.
Figure 7F:
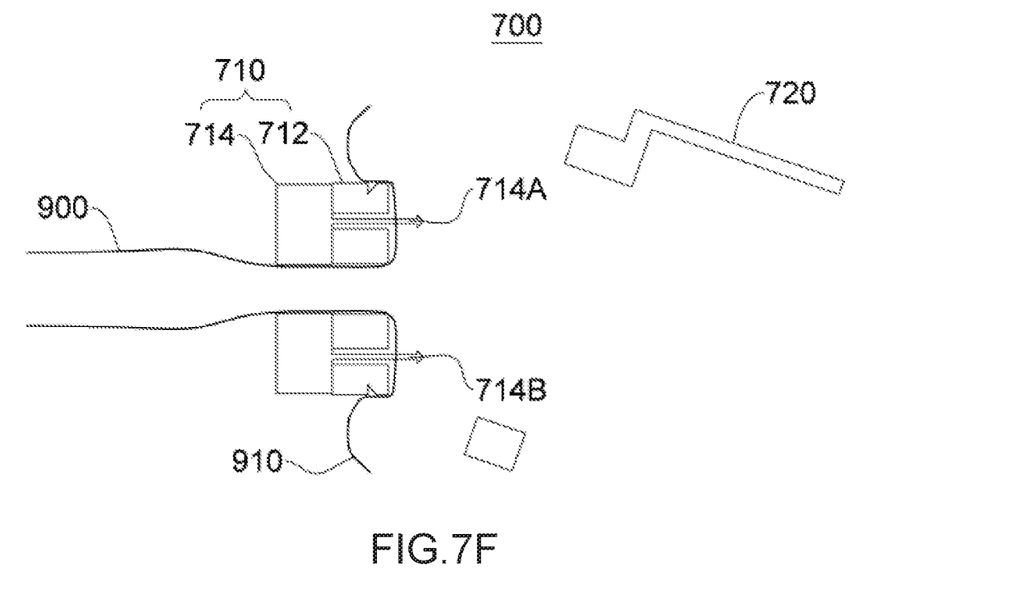
FIG. 7F is a schematic view of how to operate the blood vessel anastomosis set according to yet another specific embodiment of the present disclosure.

Referring to FIG. 7E, after the widened blood vessel cut 910 has been fitted to the blood vessel anastomosis device 710, the rear-end anastomosis portion 714 is pushed toward the front-end anastomosis portion 712; consequently, the rear-end anastomosis portion 714 abuts against the front-end anastomosis portion 712, and the anastomosis needles 714A, 714B penetrate the blood vessel cut 910. Therefore, the blood vessel cut 910 is fixed to the anastomosis needles 714A, 714B of the blood vessel anastomosis device 710. Then, the blood vessel fixation device 720 is removed from the blood vessel cut 910 (as shown in FIG. 7F). After the blood vessel fixation portion 724 has fixed the blood vessel cut 910 to the blood vessel anastomosis device 710, the anastomosis needles 714A, 714B do not protrude from the front-end anastomosis portion 712. Therefore, the anastomosis needles 714A, 714B are unlikely to be compressed by the blood vessel fixation device 720 and damaged. As soon as a first blood vessel anastomosis device and a second blood vessel anastomosis device are fixed to two blood vessel cuts, respectively, the two blood vessel cuts are connected to each other through the anastomosis needles of the first blood vessel anastomosis device and the anastomosis needles of the second blood vessel anastomosis device.

Figure 8A:
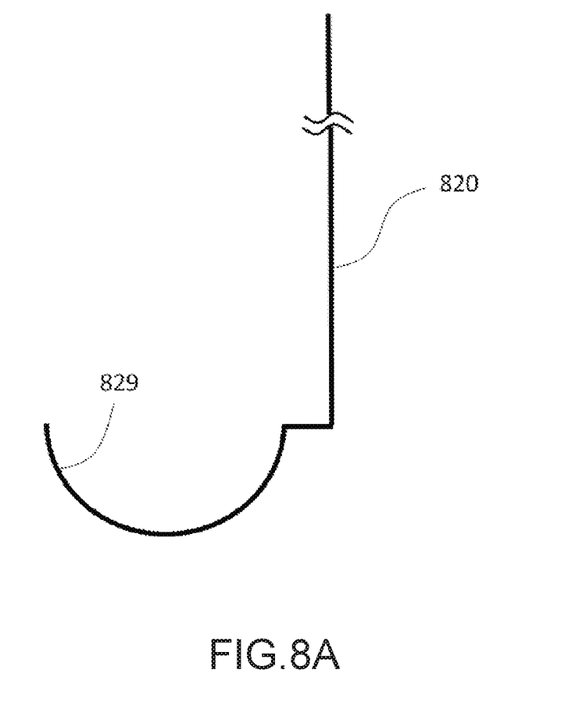
FIG. 8A is a schematic view of a blood vessel fixation device with a foldable blood vessel widening portion according to a specific embodiment of the present disclosure.

Referring to FIG. 8A, there is shown a schematic view of a blood vessel fixation device with a foldable blood vessel widening portion according to a specific embodiment of the present disclosure. In the embodiment illustrated by FIG. 8A, a foldable blood vessel widening portion 829 of a blood vessel fixation device 820 is folded, and thus the foldable blood vessel widening portion 829 enters the blood vessel cut readily.

Figure 8B:
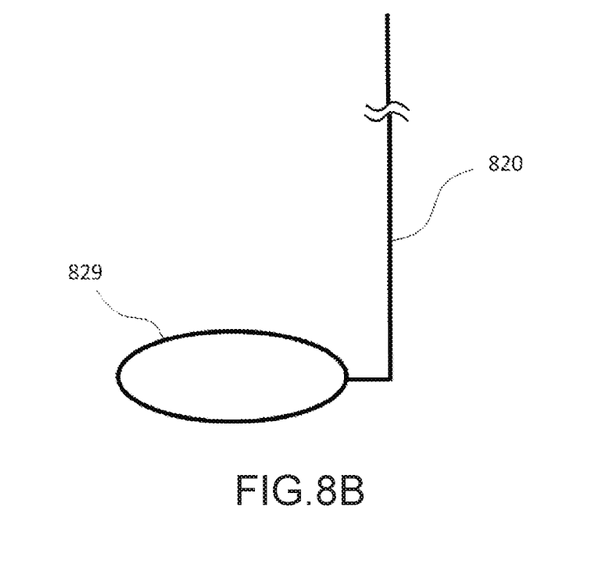
FIG. 8B is a schematic view of the blood vessel fixation device with the foldable blood vessel widening portion according to a specific embodiment of the present disclosure.

Referring to FIG. 8B, there is shown a schematic view of the blood vessel fixation device with the foldable blood vessel widening portion according to a specific embodiment of the present disclosure. In the embodiment illustrated by FIG. 8B, the foldable blood vessel widening portion 829 of the blood vessel fixation device 820 spreads. After the foldable blood vessel widening portion 829 has entered the blood vessel cut, the blood vessel fixation device 820 is manipulated in such a manner to cause the foldable blood vessel widening portion 829 to spread. Therefore, the blood vessel cut is widened with the foldable blood vessel widening portion 829, and then the widened blood vessel cut is fitted to the blood vessel anastomosis device.

The blood vessel anastomosis set of the present disclosure is also suitable for performing various anastomosis procedures on colons, small intestines, ureters, bile ducts, etc.

The blood vessel anastomosis set of the present disclosure is depicted by the accompanying drawings and described above. The specific embodiments of the present disclosure serve an exemplary purpose only. Various changes can be made to the specific embodiments of the present disclosure without departing from the claims of the present disclosure and spirit thereof and deemed falling within the scope of the claims of the present disclosure. Therefore, the specific embodiments described herein are not restrictive of the present disclosure; thus, the actual scope and spirit of the present disclosure is defined by the appended claims.

What is claimed is:

1. A blood vessel anastomosis set for anastomosing a blood vessel cut of a blood vessel, the blood vessel anastomosis set comprising:

a blood vessel anastomosis device, comprising:
   a front-end anastomosis portion; and
   a rear-end anastomosis portion having a plurality of anastomosis needles, wherein the plurality of anastomosis needles penetrate the front-end anastomosis portion, such that the rear-end anastomosis portion is movably connected to the front-end anastomosis portion through the anastomosis needles; and a blood vessel fixation device for widening the blood vessel cut to allow the blood vessel cut to be fixed to the blood vessel anastomosis device;

wherein the blood vessel fixation device comprises a blood vessel widening portion and a blood vessel fixation portion;

wherein the first blood vessel widening portion is configured to widen the blood vessel cut gradually and allows the blood vessel cut to come into contact with the blood vessel fixation portion, and thereby cause the blood vessel fixation portion fixing the blood vessel cut to the blood vessel anastomosis device;

wherein the blood vessel anastomosis device is connected through the plurality of anastomosis needles to a second blood vessel anastomosis device, wherein the second blood vessel anastomosis device is configured to fix to another blood vessel cut;

wherein the blood vessel anastomosis device has a snap-engagement portion, and the blood vessel fixation portion is disposed at the blood vessel fixation device, in which the blood vessel fixation portion is separable with the blood vessel fixation device, wherein, as soon as the blood vessel fixation portion fixes the blood vessel cut to the blood vessel anastomosis device, the blood vessel fixation portion is snap-engaged with the snap-engagement portion, and the blood vessel cut is clamped between the blood vessel fixation portion and the blood vessel anastomosis device.

2. The blood vessel anastomosis set of claim 1, wherein the plurality of anastomosis needles do not protrude from the front-end anastomosis portion when the blood vessel fixation device fixes the blood vessel cut to the blood vessel anastomosis device.

\* \* \* \* \*